(12) United States Patent
Rayhanabad

(10) Patent No.: US 12,017,032 B1
(45) Date of Patent: Jun. 25, 2024

(54) ARTERIOVENOUS GRAFT AND METHOD OF USING THEREOF

(71) Applicant: Simon B. Rayhanabad, Huntington Beach, CA (US)

(72) Inventor: Simon B. Rayhanabad, Huntington Beach, CA (US)

(73) Assignee: SBR INNOVATIONS, LLC, Huntington Beach, CA (US)

( * ) Notice: Subject to any disclaimer, the term of this patent is extended or adjusted under 35 U.S.C. 154(b) by 0 days.

(21) Appl. No.: 18/092,627

(22) Filed: Jan. 3, 2023

Related U.S. Application Data

(60) Continuation-in-part of application No. 17/163,375, filed on Jan. 30, 2021, now abandoned, and a continuation-in-part of application No. 16/536,272, filed on Aug. 8, 2019, now abandoned, which is a division of application No. 16/221,387, filed on Dec. 14, 2018, now Pat. No. 10,850,084, said application No. 17/163,375 is a continuation of application No.
(Continued)

(51) Int. Cl.
*A61M 39/02* (2006.01)
*A61M 1/14* (2006.01)
*A61M 1/36* (2006.01)
*A61M 25/00* (2006.01)

(52) U.S. Cl.
CPC .......... *A61M 39/0208* (2013.01); *A61M 1/14* (2013.01); *A61M 1/3655* (2013.01); *A61M 1/3661* (2014.02); *A61M 25/0032* (2013.01); *A61M 2025/006* (2013.01); *A61M 2039/0238* (2013.01)

(58) Field of Classification Search
CPC .... A61M 1/14; A61M 1/3655; A61M 1/3661; A61M 25/0032; A61M 39/0208; A61M 2025/006; A61M 2039/0238
See application file for complete search history.

(56) References Cited

U.S. PATENT DOCUMENTS

| | | |
|---|---|---|
| 3,713,441 A | 1/1973 | Thomas |
| 3,818,511 A | 6/1974 | Goldberg |
| 5,849,036 A | 12/1998 | Zarate |

(Continued)

FOREIGN PATENT DOCUMENTS

WO    WO2016111642    7/2016

OTHER PUBLICATIONS

Jennings et al., The Venous Window Needle Guide, a hemodialysis cannulation device for salvage of uncannulatablearteriovenous fistulas, Journal of vascular surgery, vol. 60, Issue 4, pp. 1024-1032, Oct. 2014.

*Primary Examiner* — Benjamin J Klein
(74) *Attorney, Agent, or Firm* — Steven R. Vosen

(57) ABSTRACT

An arteriovenous graft (AV graft) and method of using the AV graft to facilitate dialysis is described. The AV graft includes a tube having two or more embedded reinforcing elements that each extend along a length of the tube and extends circumferentially along a portion of the tube. The reinforcing element is positioned in the patent distal to the skin and assists by minimizing slippage of a hemodialysis needle that might happen to attempt to pierce the back side of the AV graft. The method includes providing the AV graft to the patient and providing hemodialysis to a patient provided with the AV graft.

21 Claims, 4 Drawing Sheets

Related U.S. Application Data

16/186,555, filed on Nov. 11, 2018, now Pat. No. 10,905,856.

(60) Provisional application No. 63/296,114, filed on Jan. 3, 2022, provisional application No. 62/673,766, filed on May 18, 2018, provisional application No. 62/634,663, filed on Feb. 23, 2018, provisional application No. 62/599,449, filed on Dec. 15, 2017, provisional application No. 62/599,441, filed on Dec. 15, 2017, provisional application No. 62/585,490, filed on Nov. 13, 2017.

(56) References Cited

U.S. PATENT DOCUMENTS

| | | | |
|---|---|---|---|
| 6,146,414 A | 11/2000 | Gelman | |
| 6,206,913 B1 | 3/2001 | Yencho | |
| 6,261,257 B1 * | 7/2001 | Uflacker | A61M 1/3655 604/9 |
| 6,416,537 B1 | 7/2002 | Martakos | |
| 7,828,781 B2 | 11/2010 | Edoga | |
| 8,313,524 B2 | 11/2012 | Edwin | |
| 10,850,084 B1 * | 12/2020 | Rayhanabad | A61M 25/0032 |
| 2003/0100920 A1 | 5/2003 | Akin | |
| 2004/0102796 A1 | 5/2004 | Hill | |
| 2005/0171565 A1 | 8/2005 | Yencho | |
| 2008/0176271 A1 | 7/2008 | Silver | |
| 2008/0255609 A1 | 10/2008 | Opie | |
| 2009/0035346 A1 | 2/2009 | Nugent | |
| 2009/0157014 A1 * | 6/2009 | Osborne | A61M 39/04 604/513 |
| 2010/0056978 A1 | 3/2010 | Machan | |
| 2010/0204783 A1 | 8/2010 | Nugent | |
| 2011/0213309 A1 | 9/2011 | Young | |
| 2012/0245536 A1 | 9/2012 | Gerber | |
| 2013/0274648 A1 | 10/2013 | Weinberger | |
| 2014/0018721 A1 * | 1/2014 | Gage | A61M 39/0247 604/8 |
| 2017/0304092 A1 | 10/2017 | Hong | |
| 2018/0289939 A1 | 10/2018 | Mason | |
| 2022/0323662 A1 * | 10/2022 | Glowczwski | A61M 39/0208 |
| 2024/0001098 A1 * | 1/2024 | Glowczwski | A61M 1/3655 |

\* cited by examiner

ARTERIOVENOUS GRAFT AND METHOD OF USING THEREOF

CROSS-REFERENCE TO RELATED APPLICATIONS

This application claims the benefit of U.S. Provisional Application No. 63/296,114 filed Jan. 3, 2022. This application is also a continuation-in-part of U.S. patent application Ser. No. 16/536,272 filed Aug. 8, 2019, which is a divisional of U.S. patent application Ser. No. 16/221,387 filed Dec. 14, 2018 which issued on Dec. 1, 2020 as U.S. Pat. No. 10,850,084, which claims the benefit of U.S. Provisional Application No. 62/599,449 filed Dec. 15, 2017. This application is also a continuation-in-part of application Ser. No. 17/163,375 filed Jan. 30, 2021, which is a continuation of U.S. patent application Ser. No. 16/186,555 filed Nov. 11, 2018 which issued on Feb. 2, 2021 as U.S. Pat. No. 10,905,856, which claims the benefit of U.S. Provisional Application No. 62/585,490 filed Nov. 13, 2017, U.S. Provisional Application No. 62/599,441 filed Dec. 15, 2017, U.S. Provisional Application No. 62/634,663 filed Feb. 23, 2018, and U.S. Provisional Application No. 62/673,766 filed May 18, 2018. The contents of all of the patents referred to in this paragraph are hereby incorporated by reference in their entirety.

BACKGROUND OF THE INVENTION

Field of the Invention

The present invention generally relates medical devices and their use, and more specifically to an arteriovenous graft and a method of using an arteriovenous graft.

Discussion of the Background

BACKGROUND

In hemodialysis, an artificial kidney is used to remove waste and extra chemicals and fluid from a patient's blood. Typically, blood is removed from a first location in the patient's circulation system, is filtered, and is provided back into the patient at a second location that is downstream from the first location.

Vascular access is obtained from a minor surgical procedure to the arm or leg. In some cases, an access is obtained by joining an artery to a vein to form a bigger blood vessel to form a fistula.

The nature of hemodialysis requires vascular access that is suitable for repeated puncture and allows a high blood flow rate for high-efficiency hemodialysis with minimal complications. Over time, however, complications may arise, due in part to the weakening of the blood vessels due to repeated puncturing.

There is a need in the art for an arteriovenous graft that extends the life of vascular access for hemodialysis.

BRIEF SUMMARY OF THE INVENTION

The present invention overcomes the disadvantages of prior art by providing an arteriovenous graft (an "AV graft") having a reinforcing element embedded in the AV graft.

It is one aspect to provide an AV graft comprising: a tube formed from a biocompatible material, where the tube has a lumen extending a length between a first end and a second end; and two or more reinforcing elements, where each of the two or more reinforcing elements is embedded in the tube, where each of the two or more reinforcing elements extends partially around a circumference of the tube and extends along a different portion of the length of the tube from other reinforcing elements of the two or more reinforcing elements, and where a side of at least one reinforcing element of the two or more reinforcing elements facing the lumen includes one or more surface features. The AV graft is such that if a tip of a needle inserted through the tube adjacent to one of the two or more reinforcing element and contacts the one or more surface features, the tip of the needle is inhibited or prevented from moving along the reinforcing element and from puncturing the reinforcing elements.

It is another aspect to provide an AV graft with two reinforcing elements including a first reinforcing element and a second reinforcing element, and where the tube includes, sequentially: a first end portion, where the first end portion is flexible and includes the first end, a first reinforced portion including the first reinforcing element; a central portion, where the central portion is flexible; a second reinforced portion including the second reinforcing element; and a second end portion, where the second end portion is flexible and includes the second end.

It is one aspect to provide a method for using an AV graft with a patient. The AV graft includes a tube formed from a biocompatible material, where the tube has a lumen extending a length between a first end and a second end, an inner surface, and an outer surface; and two or more reinforcing elements, where each of the two or more reinforcing elements is embedded in the tube, where each of the two or more reinforcing elements extends partially around a circumference of the tube and extends along a different portion of the length of the tube from other reinforcing elements of the two or more reinforcing elements, and where a side of at least one reinforcing element of the two or more reinforcing elements facing the lumen includes one or more surface features, such that if a tip of a needle inserted through the tube adjacent to one of the two or more reinforcing element and contacts the one or more surface features, the tip of the needle is inhibited or prevented from moving along the reinforcing element and from puncturing the reinforcing elements. The method includes: incising the patient to provide access to an artery and a vein; attaching the first end of the AV graft to the artery; attaching the second end of the AV graft to the vein; and surgically providing the attached AV graft below a surface of a skin of the patient, such that the attached AV graft below the surface of the skin is oriented with the reinforcing element distal to the skin.

It is yet another aspect to provide a method for providing hemodialysis to a patient using an AV graft. The AV graft includes a tube formed from a biocompatible material, where the tube has a lumen extending a length between a first end and a second end, an inner surface, and an outer surface; and two or more reinforcing elements, where each of the two or more reinforcing elements is embedded in the tube, where each of the two or more reinforcing elements extends partially around a circumference of the tube and extends along a different portion of the length of the tube from other reinforcing elements of the two or more reinforcing elements, and where a side of at least one reinforcing element of the two or more reinforcing elements facing the lumen includes one or more surface features, such that if a tip of a needle inserted through the tube adjacent to one of the two or more reinforcing element and contacting the one or more surface features, the tip of the needle is inhibited or prevented from moving along the reinforcing element and from puncturing the reinforcing elements, and where the AV graft is positioned below the surface of a skin of the patient, and oriented with the reinforcing element distal to the skin. The method includes: inserting a first needle connected to a catheter of a hemodialysis machine through the skin of a patient and into the AV graft and towards the first reinforcing element of the two or more reinforcing elements, inserting a second needle connected to a second catheter of a hemodialysis machine through the skin of a patient and into the AV graft and towards the second reinforcing element of the two or more reinforcing elements, and providing hemodialysis to the patient.

These features together with the various ancillary provisions and features which will become apparent to those skilled in the art from the following detailed description, are attained by the AV graft and method of using an AV graft of the present invention, preferred embodiments thereof being shown with reference to the accompanying drawings, by way of example only, wherein:

Reference symbols are used in the Figures to indicate certain components, aspects or features shown therein, with reference symbols common to more than one Figure indicating like components, aspects or features shown therein.

DETAILED DESCRIPTION OF THE INVENTION

Embodiments are presented for an AV graft that may be used to providing hemodialysis to a patient. The AV graft includes tube formed from a flexible biocompatible material and includes a rigid portion that extends over a portion of the tube. The AV graft may be provided under the surface of the skin of the patent in preparation for hemodialysis. The rigid portion acts to inhibit or prevent a hemodialysis needle inserted into the AV graft from slipping along the AV graft and/or from puncturing the opposite side of the AV graft.

Figure 1:
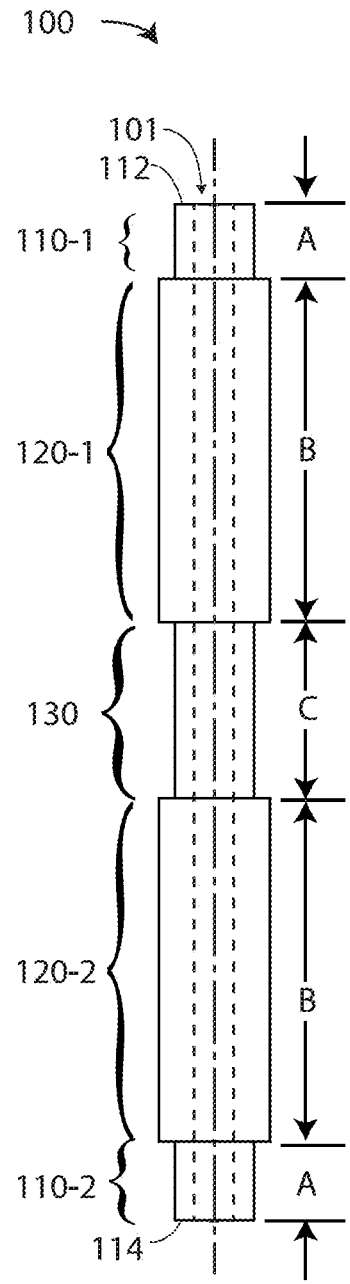
FIG. 1 is a side view of a first embodiment AV graft.

FIG. 1 is a side view of a first embodiment AV graft 100. AV graft 100 is a tube with a lumen 101 that extends from a first end 112 to a second end 114. AV graft 100 further includes several portions including two end portions 110, a central portion 130, and two reinforced portions 120. The two end portions 110 are shown as end portion 110-1 and end portion 110-2, where end portion 110-1 includes first end 112 and where end portion 110-2 include second end 114. The two reinforced portions 120 are shown as reinforced portion 120-1 and reinforced portion 120-2. In general, end portions 110 and central portion 130 are flexible and reinforced portion 120 is rigid, and thus the length of AV graft 100 alternates between flexible and rigid portions.

Figure 3A:
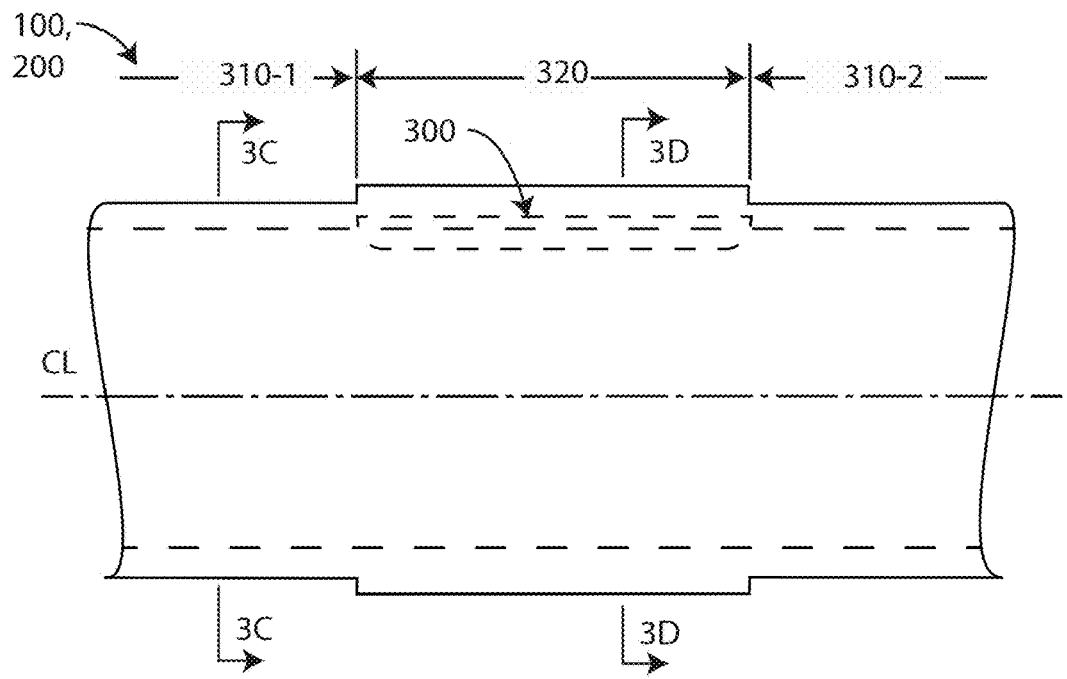
FIGS. 3A, 3B, 3C, and 3D are a side view, a top view, a first sectional view 3C-3C, and a second sectional view 3D-3D, respectively, of one embodiment of an AV graft.
Figure 3B:
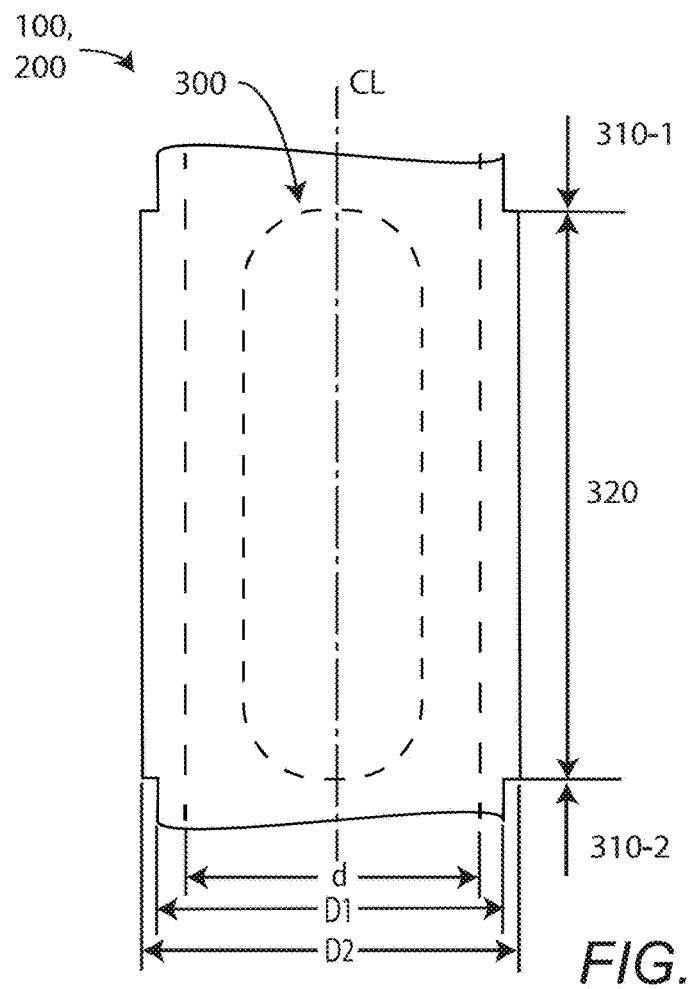
Figure 3C:
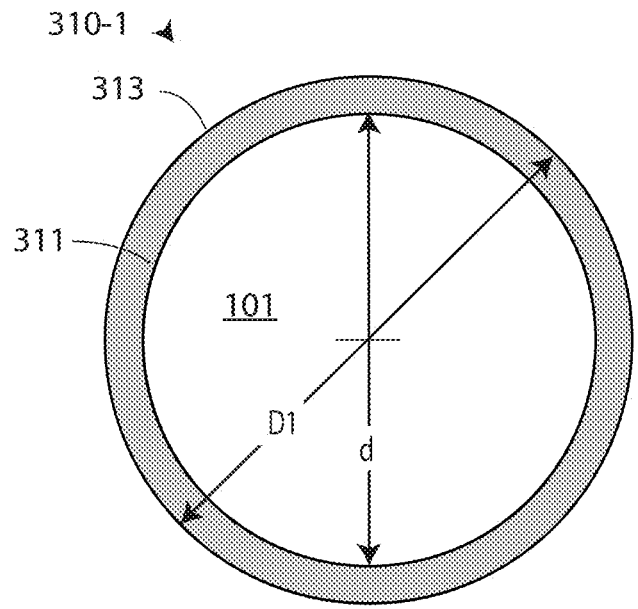

FIG. 3A as a side view of a portion of AV graft 100 showing a reinforced portion 320 and two adjacent portions 310. shown as a portion 310-1 and as a portion 310-2, FIG. 3B as a top view of the embodiment of FIG. 3A, FIG. 3C is a sectional view 3C-3C of portion 310-1, and FIG. 3C is a sectional view 3D-3D of portion 320. With reference to FIG. 1, portion 310-1 is end portion 110 and portion 310-2 is central portion 130.

Figure 3D:
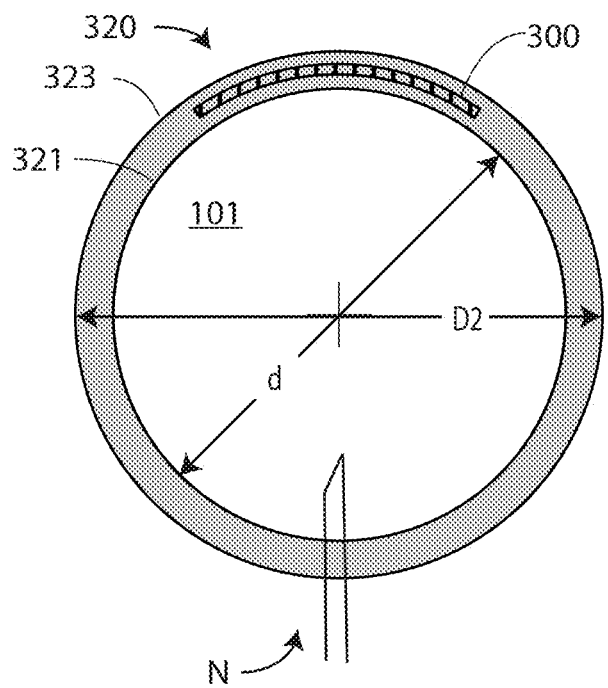

As shown in FIGS. 3B, 3C, and 3D, portions 310 and 320 have inner surfaces 311 and 321, respectively, which have a diameter d and which form portions of lumen 101, portion 310 has an outer surface 313, and portion 320 has an outer surface 313. Outer surface 313 is shown illustratively as having a diameter D1 and outer surface 323 is shown illustratively as having a diameter D2. In general portions 310 and 320 may have different structures or features on their respective outer surfaces 313 and 323, and thus may not be cylindrical, as shown in the Figures, or they may have the same outer diameter. In other embodiments, diameter D1 and/or diameter D2 may vary along the length of portion 310 and/or portion 320, respectively.

In general, portions 310 (for example and without limitation, either one of end portions 110 and central portion 130) are flexible and may constructed, for example and without limitation, from a biocompatible material, such as stretched polytetrafluoroethylene (PTFE), such as GORE-TEX® Vascular Graft (manufactured by W. L. Gore & Associates, Inc., Medical Products Division, Flagstaff, AZ), as are known in the art.

In general, reinforced portions 320 (for example and without limitation reinforced portion 120) may, for example and without limitation, include the material of portion 310, which for example and without limitation may be a stretched PTFE and also includes a reinforcing element 300 embedded in reinforcing portion 320 and which extends partially around the circumference of reinforced portions 320. Reinforcing element 300 may, for example and without limitation, be formed from PTFE formed into a fabric, such as Gore-Tex (W. L. Gore and Associates, Newark, Del.), or a metal such as stainless steel or titanium, and may for example and without limitation, be embedded within the stretched PTFE.

Reinforcing elements 300 disclosed herein are examples of certain reinforcing elements. Examples of other reinforcing element include, for example and without limitation, the patches described in the following co-owned US Patents and US Patent Applications, the contents of which are hereby incorporated by reference: U.S. Pat. No. 10,905,856 issued on Feb. 2, 2021, U.S. Pat. No. 11,389,622 issued on Jul. 19, 2022, and U.S. patent application Ser. No. 17/163,375 filed on Jan. 30, 2021, which published as US Patent Application Publication No 20210275780 on Sep. 9, 2021.

As shown in FIG. 1, the length of end portions 110-1 and 110-2 is A, the length of reinforced portions 120-1 and 120-2 is B, and the length of central portion 120 is C. In certain embodiments, the length A is from 3-6 cm, the length B is from 3 cm to 7 cm, and the length C is from 1 cm to 61 cm. The total length of AV graft 100 is thus from 10 cm to 80 cm.

In general, the shape of end portions 110 and central portion 120 are the tubular or may be arranged to have a generally cylindrical shape, which includes a cylindrical shape or a cylindrical shape with features on one or more of inner surface 311, inner surface 321, outer surface 313, or outer surface 323. In certain other embodiments, the diameter d of lumen 101 is from 5 mm to 24 mm. In certain other embodiments, the thickness of portions 110, 120, or 130 is from ¼ mm to 1 mm, and thus the diameter D1 or D2 may vary from 5.25 mm and 25 mm.

In alternative embodiments end portions 110-1 and 110-2 may have different shapes and/or dimensions or may be formed from different biocompatible materials, and/or reinforced portions 120-1 and 120-2 may have different shapes and/or dimensions or may be formed from different biocompatible materials or have different reinforcing elements 300.

Figure 2:
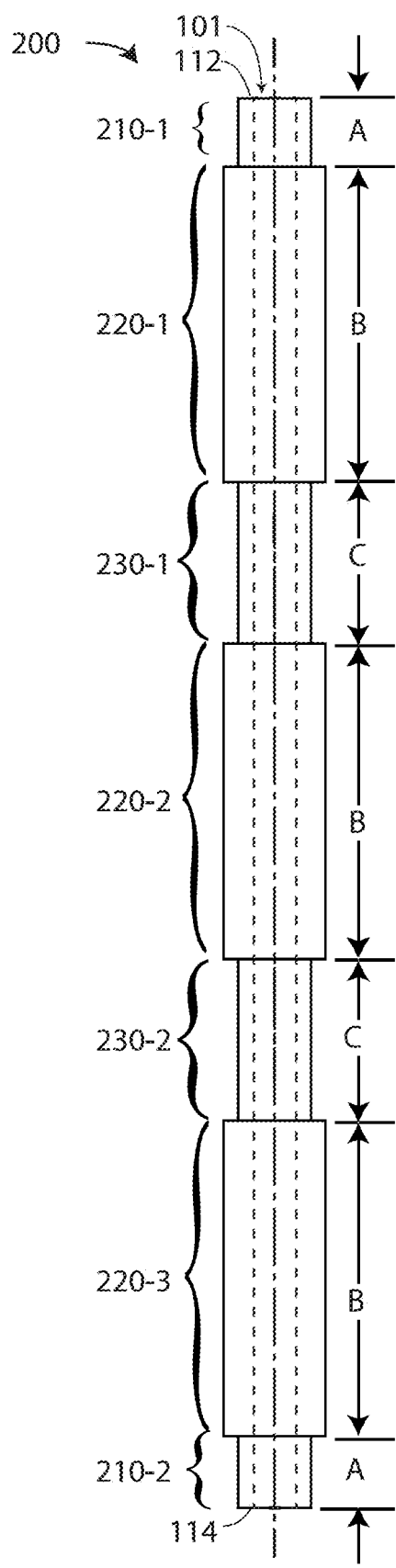
FIG. 2 is a side view of a second embodiment AV graft.

A second embodiment AV graft 200 is shown in the side view of FIG. 2 and in FIGS. 3A-3D. AV graft 200 is substantially the same as AV graft 100, except as explicitly noted.

AV graft 200 includes two end portions 210, shown as end portion 210-1 and end portion 210-2, two central portions 230 shown as a central portion 230-1 and a central portion 230-1, and three reinforced portions 220 shown as a reinforced portion 220-1, a reinforced portions 220-2, and a reinforced portion 220-3. End portions 210 are generally similar to end portions 110 and central portions 230 are generally similar to central portions 130, with both the end portions and central portions shown in FIGS. 3A, 3B. and 3C as portion 310. Reinforced portions 220 are generally similar to reinforced portion 120 and are shown as portion 320 in FIGS. 3A, 3B, and 3D. In general, end portions 210 and central portions 230 are flexible and reinforced portions 220 are rigid, and thus the length of AV graft 200 alternates between flexible and rigid portions.

In alternative embodiments end portions 210-1 and 210-2 may have different shapes and/or dimensions or may be formed from different biocompatible materials, central portions 230-1 and 230-2 may have different shapes and/or dimensions or may be formed from different biocompatible materials, and/or reinforced portions 220-1, 220-2, and 220-3 may have different shapes and/or dimensions or may be formed from different biocompatible materials or have different reinforcing elements 300.

In certain embodiments, AV graft 100 or AV graft 200 is formed by first manufacturing reinforcing element 300, and then introducing the reinforcing element into the manufacturing of the AV graft. Thus, for example, a PTFE AV graft may be manufactured by depositing layers of PTFE on a mandrel. After initial layers of PTFE are deposited, reinforcing element 300 is placed on the deposited PTFE, and additional layers of PTFE are added. As a result, reinforcing element 300 is embedded within the AV graft.

FIGS. 4A, 4B, 4C, and 4D are a top, a side, a bottom, and an end view of several embodiments of reinforcing element 300 which forms a rigid portion of AV graft 100 or of AV graft 200. Reinforcing element 300 has, in general, an outer surface 401 and inner surface 402. In one embodiment, the material of reinforcing element 300 is a biocompatible material, such as polytetrafluoroethylene (PTFE), formed into a fabric, such as Gore-Tex (W. L. Gore and Associates, Newark, Delaware), or a metal, such as a stainless steel or titanium. In general, reinforcing element 300 is rigid enough to prevent puncturing by a needle.

In certain embodiments, outer surface 401 and inner surface 402 are a portion of a generally cylindrical shape, which includes a portions of a cylindrical shape or portions of a cylindrical shape having features on the outer surface and/or on the inner surface.

In certain embodiments, reinforcing element 300 has a thickness of from between 0.5 mm to 1.0 mm with a longitudinal length, L, between 3 cm to 7 cm. In certain embodiments, the width of reinforcing element 300 is such that it covers an angle, ∂, about a diameter that is in the range of from 70 degrees to 180 degrees. In certain other embodiments, the angle, ∂, is from 70 degrees to 90 degrees, from 90 degrees to 120 degrees, from 120 degrees to 150 degrees, or from 150 degrees to 180 degrees. In other embodiments, ∂ is 70 degrees, 80 degrees, 90 degrees, 100 degrees, 110 degrees, 120 degrees, 130 degrees, 140 degrees, 150 degrees, 160 degrees, 170 degrees, or 180 degrees.

Figures 4A, 4B, 4C:
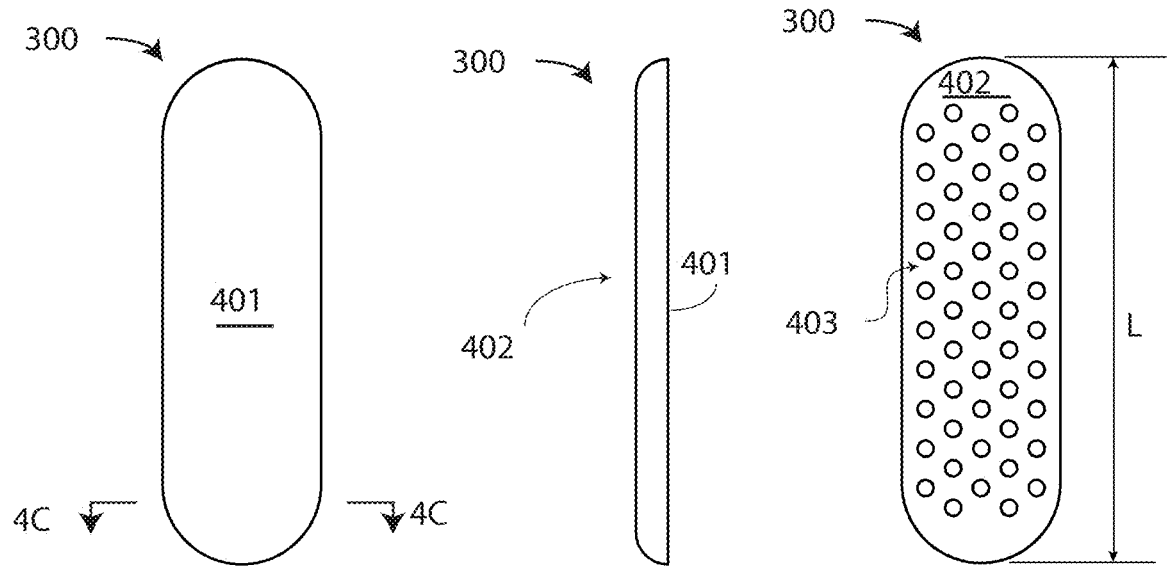
FIGS. 4A, 4B, 4C, 4D, and 4E are a top, a side, a bottom, an end view, and a sectional view 4E-4E of one embodiment of a rigid portion that is embedded in the AV graft.
Figures 4D, 4E:
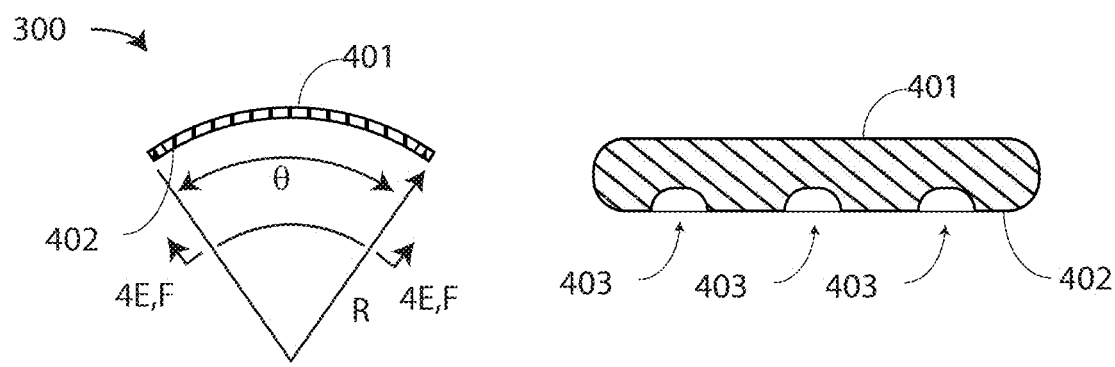
Figure 4F:
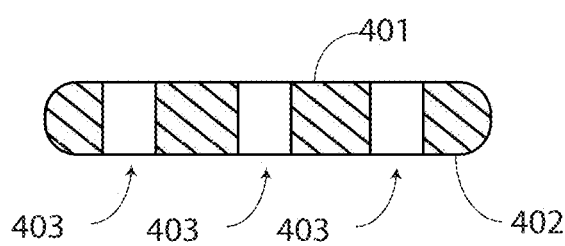
FIG. 4F is a sectional view 4F-4F of an alternative rigid portion that is embedded in the AV graft.

FIG. 4E is an embodiment of reinforcing element 300 including three-dimensional features 403 which may be a roughened surface, or a surface covered with holes or protuberances, and FIG. 4F is a sectional view 4F-4F of FIG. 4D illustrating an alternative embodiment of the reinforcement element 300, where three-dimensional features 403 include holes that extend through the thickness of reinforcement element 300.

Three-dimensional features 403 may be, for example and without limitation, a roughened surface, and/or a surface covered with holes or protuberances as shown in FIG. 4E. In certain embodiments, the holes have a diameter selected to inhibit or prevent a needle from moving along the inner surface. Three-dimensional features 403 may be of the same size and arranged in a regular pattern, as shown in FIG. 4C with similar feature sizes d. In certain embodiments, feature size d is on the order of the size of a catheter needle, such as that of a 15 gauge needle, which has a diameter of 1.829 mm, a 16 gauge needle, which has a diameter of 1.651 mm, a 17 gauge needle, which has a diameter of 1.473 mm or a 18 gauge needle, which has a diameter of 1.27 mm.

In various other embodiments, at least some of the feature sizes d are 1 mm, are 2 mm, are 4 mm, or are 8 mm. In yet other embodiments, feature sizes d include features ranging in size from 1 mm to 2 mm, from 2 mm to 3 mm, from 3 mm to 4 mm, from 4 mm to 5 mm, or from 5 mm to 6 mm. Alternatively, for example and without limitation, three-dimensional features 403 may have a diameter, without limitation, of from 0.25 mm to 2 mm, such as, for example 1.0 mm, or otherwise sized to engage with the tip of a needle, such as a 15 gauge needle, a 16 gauge needle, a 17 gauge needle, or a 18 gauge needle.

Alternatively, or in addition to the roughened surface, and/or a surface covered with holes or protuberances of FIG. 4E, the three-dimensional features 403 may be, or also include holes having the size and distribution discussed above, where the holes extend through the thickness of reinforcement element 300.

To provide hemodialysis, a needle, N, as shown in FIG. 3D, is inserted through AV graft 100 or 200 and into lumen 101. Importantly, the needle is positioned such that reinforcing element 300 is distal to where the needle enters lumen 101. Alternatively, the healthcare provider may palpate the skin to find the location of AV graft 100. This allows the person inserting the needle into the patient to determine the location of AV graft 100, and thus makes it easier to inert the needle at the proper location. Once the needle is inserted, hemodialysis may be provided to the patient.

One method of providing the AV graft 100 to a patient is by: 1) incising the patient to provide access to an artery and a vein; 2) attaching first end 112 to the artery; 3) attaching second end 114 to the vein; and 4) surgically providing the attached AV graft below the surface of the skin of the patient, such that the attached AV graft below the surface of the skin is oriented with the reinforcing element distal to the skin.

One method of providing hemodialysis to a patient using an AV graft having AV graft 100 provided, as by the previous paragraph for example, is by: 1) inserting a first needle connected to the catheter of a hemodialysis machine through the skin of a patient and into the AV graft and towards the reinforcing element of one of reinforced portion 320, 1) inserting a second needle connected to the catheter of a hemodialysis machine through the skin of a patient and into the AV graft and towards the reinforcing element of another reinforced portion 320, and 3) providing hemodialysis to the patient.

Reference throughout this specification to "one embodiment" or "an embodiment" means that a particular feature, structure, or characteristic described in connection with the embodiment is included in at least one embodiment of the present invention. Thus, appearances of the phrases "in one embodiment" or "in an embodiment" in various places throughout this specification are not necessarily all referring to the same embodiment. Furthermore, the particular features, structures or characteristics may be combined in any suitable manner, as would be apparent to one of ordinary skill in the art from this disclosure, in one or more embodiments.

Similarly, it should be appreciated that in the above description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description are hereby expressly incorporated into this Detailed Description, with each claim standing on its own as a separate embodiment of this invention.

Thus, while there has been described what is believed to be the preferred embodiments of the invention, those skilled in the art will recognize that other and further modifications may be made thereto without departing from the spirit of the invention, and it is intended to claim all such changes and modifications as fall within the scope of the invention.

I claim:

1. An arteriovenous graft (AV graft) comprising:
a tube formed from a biocompatible material, where said tube has a lumen extending a length between a first end and a second end; and
two or more reinforcing elements, where each of the two or more reinforcing elements is embedded in the tube, where each of the two or more reinforcing elements extends partially around a circumference of the tube and extends along a different portion of the length of the tube from other reinforcing elements of the two or more reinforcing elements, and where a side of at least one reinforcing element of the two or more reinforcing elements facing the lumen includes one or more surface features,
such that if a tip of a needle inserted through the tube adjacent to one of the two or more reinforcing element and contacts the one or more surface features, the tip of the needle is inhibited or prevented from moving along the reinforcing element and from puncturing the reinforcing elements.

2. The AV graft of claim 1, where the tube includes stretched polytetrafluoroethylene (PTFE).

3. The AV graft of claim 1, where the tube has a generally cylindrical shape.

4. The AV graft of claim 1, where the lumen is between 5 mm and 24 mm.

5. The AV graft of claim 1, where said reinforcing element includes polytetrafluoroethylene (PTFE) or a metal, and where said metal includes stainless steel or titanium.

6. The AV graft of claim 1, where the side has a generally cylindrical shape.

7. The AV graft of claim 1, where a thickness of the reinforcing element is between 0.5 mm and 1.0 mm.

8. The AV graft of claim 1, where said length of said reinforcing element is between 3 cm and 7 cm.

9. The AV graft of claim 1, where a width of said reinforcing element extends partially around the circumference of the tube by between 70 degrees to 180 degrees.

10. The AV graft of claim 1, where the length of AV graft is between 10 cm and 80 cm.

11. The AV graft of claim 1, where said one or more surface features include a roughened surface, one or more protuberances on the surface, or a plurality of holes through the reinforcing element.

12. The AV graft of claim 1, where at some of said one or more surface features are a size of the tip of a catheter needle.

13. The AV graft of claim 12, where the catheter needle is a 15 gauge needle, a 16 gauge needle, a 17 gauge needle, or a 18 gauge needle.

14. The AV graft of claim 1, where at some of the one or more surface features are between from 0.25 mm and 2 mm, between 1 mm and 2 mm, between 2 mm and 3 mm, between 3 mm and 4 mm, between 4 mm and 5 mm, or between 5 mm and 6 mm.

15. The AV graft of claim 1, where said two or more reinforcing elements are two reinforcing elements including a first reinforcing element and a second reinforcing element.

16. The AV graft of claim 1, where said two or more reinforcing elements are three elements including a first reinforcing element, a second reinforcing element, and a third reinforcing element.

17. The AV graft of claim 15, where said tube includes, sequentially:
a first end portion, where the first end portion is flexible and includes the first end;
a first reinforced portion including the first reinforcing element;
a central portion, where the central portion is flexible;
a second reinforced portion including the second reinforcing element; and
a second end portion, where the second end portion is flexible and includes the second end.

18. The AV graft of claim 15, where said tube includes, sequentially:
a first end portion, where the first end portion is flexible and includes the first end;
a first reinforced portion including the first reinforcing element;
a first central portion, where the first central portion is flexible;
a second reinforced portion including the second reinforcing element;
a second central portion, where the second central portion is flexible;
a third reinforced portion including the third reinforcing element; and
a second end portion, where the second end portion is flexible and includes the second end.

19. A method for using an arteriovenous graft (AV graft) with a patient, where said AV graft includes a tube formed from a biocompatible material, where said tube has a lumen extending a length between a first end and a second end, an inner surface, and an outer surface; and two or more reinforcing elements, where each of the two or more reinforcing elements is embedded in the tube, where each of the two or more reinforcing elements extends partially around a circumference of the tube and extends along a different portion of the length of the tube from other reinforcing elements of the two or more reinforcing elements, and where a side of at least one reinforcing element of the two or more reinforcing elements facing the lumen includes one or more surface features, such that if a tip of a needle inserted through the tube adjacent to one of the two or more reinforcing element and contacts the one or more surface features, the tip of the needle is inhibited or prevented from moving along the reinforcing element and from puncturing the reinforcing elements, said method comprising:

incising the patient to provide access to an artery and a vein;

attaching the first end of the AV graft to the artery;

attaching the second end of the AV graft to the vein; and surgically providing the attached AV graft below a surface of a skin of the patient, such that the attached AV graft below the surface of the skin is oriented with the reinforcing element distal to the skin.

20. A method of claim 19 further comprising:

inserting a first needle connected to a catheter of a hemodialysis machine through the skin of a patient and into the AV graft and towards the first reinforcing element of the two or more reinforcing elements, inserting a second needle connected to a second catheter of a hemodialysis machine through the skin of a patient and into the AV graft and towards the second reinforcing element of the two or more reinforcing elements, and providing hemodialysis to the patient.

21. A method for providing hemodialysis to a patient using an arteriovenous graft (AV graft), where said AV graft includes a tube formed from a biocompatible material, where said tube has a lumen extending a length between a first end and a second end, an inner surface, and an outer surface; and two or more reinforcing elements, where each of the two or more reinforcing elements is embedded in the tube, where each of the two or more reinforcing elements extends partially around a circumference of the tube and extends along a different portion of the length of the tube from other reinforcing elements of the two or more reinforcing elements, and where a side of at least one reinforcing element of the two or more reinforcing elements facing the lumen includes one or more surface features, such that if a tip of a needle inserted through the tube adjacent to one of the two or more reinforcing element and contacting the one or more surface features, the tip of the needle is inhibited or prevented from moving along the reinforcing element and from puncturing the reinforcing elements, and where the AV graft is positioned below the surface of a skin of the patient, and oriented with the reinforcing element distal to the skin, said method comprising:

inserting a first needle connected to a catheter of a hemodialysis machine through the skin of a patient and into the AV graft and towards the first reinforcing element of the two or more reinforcing elements, inserting a second needle connected to a second catheter of a hemodialysis machine through the skin of a patient and into the AV graft and towards the second reinforcing element of the two or more reinforcing elements, and providing hemodialysis to the patient.

\* \* \* \* \*